United States Patent [19]

Tan et al.

[11] Patent Number: 4,886,910

[45] Date of Patent: Dec. 12, 1989

[54] CYANOGUANIDINE DERIVATIVE AND PROCESS FOR PREPARATION THEREOF

[75] Inventors: Hiroaki Tan, Otake; Koji Kato, Waki; Junichi Imuta, Otake; Noriaki Kihara, Iwakuni, all of Japan

[73] Assignee: Mitsui Petrochemical Industries, Ltd., Tokyo, Japan

[21] Appl. No.: 156,658

[22] Filed: Feb. 17, 1988

[30] Foreign Application Priority Data

Feb. 17, 1987 [JP] Japan .................................. 62-32327

[51] Int. Cl.$^4$ ........................................... C07B 103/44
[52] U.S. Cl. .................................................. 564/215
[58] Field of Search ........................................ 564/215

[56] References Cited

U.S. PATENT DOCUMENTS 4,276,421 6/1981 Baudet ................................ 564/240

FOREIGN PATENT DOCUMENTS 455991 2/1978 Spain ................................... 564/240

Primary Examiner—James H. Reamer
Attorney, Agent, or Firm—Sherman and Shallow

[57] ABSTRACT

The present invention provides a cyanoguanidine derivative which is a precursor for the synthesis of N-cyano-N'-methyl-N''-[2-{(5-methyl-1H-imidazol-4-yl)methylothio}ethyl]-guanidine (Cimetidine) or its relted compound, which has an action of controlling secretion of acid in the stomach based on the histamine $H_2$ receptor antagonism and is valuable as a drug for treating gastric ulcer. This cyanoguanidine derivative is prepared by reacting a haloketone derivative with an ammonium salt and a lower fatty acid salt or by reacting other cyanoguanidine derivative with an ammonium salt.

4 Claims, No Drawings

CYANOGUANIDINE DERIVATIVE AND PROCESS FOR PREPARATION THEREOF

BACKGROUND OF THE INVENTION (1) Field of the Invention

The present invention relates to a precursor for the synthesis of Cimetidine which has an action of controlling secretion of acid in the stomach based on the histamine $H_2$ receptor antagonism and is valuable as a drug for treating gastric ulcer, and a process for the preparation of this precursor.

(2) Description of the Prior Art

Imidazole derivatives such as 4-hydroxymethyl-5-methylimidazole disclosed in Japanese patent application laid-open specification No. 142271/81, 4-(2-aminoethylthio)-5-methylimidazole disclosed in Japanese patent application laid-open specification No. 42661/72 and [(4-methyl-5-imidazolyl)methylthioethyl]-S-methylisothiourea disclosed in Japanese patent application laid-open specification No. 75574/74 are mainly known as the precursor for the synthesis of Cimetidine and Cimetidine can be derived from these imidazole derivatives. As the precursor that can be converted to Cimetidine by forming an imidazole ring at the final stage, there can be mentioned N-cyano-N'-2-(2,3-diketobutylthio)ethyl-N''-methylguanidine disclosed in Spanish Pat. No. 455,991 [Chemical Abstracts, 89, 146904 I, 1978]. Diacetyl which is the starting material for the synthesis of this precursor has an offensive smell and causes a problem concerning the working environment, and the yield of the precursor is not always high.

SUMMARY OF THE INVENTION

We made investigations with a view to developing a reasonable Cimetidine-preparing process having a reduced number of reaction stages and simplifying operations. As the result, we found a novel cyanoguanidine derivative which is quite different from the above-mentioned compounds disclosed in the literature references. Accordingly, the present invention provides this novel cyanoguanidine derivative and a process for the preparation of this novel cyanoguanidine derivative.

This cyanoguanidine derivative can be efficiently converted to Cimetidine in a high yield, for example, by reacting the cyanoguanidine derivative in formamide at about 100° C. in the presence of ammonium formate, sodium ammonium hydrogenphosphate tetrahydrate and methyl orthoformate.

More specifically, the present invention relates to a novel cyanoguanidine derivative and a process for the preparation thereof. The novel cyanoguanidine derivative is represented by the following formula (I):

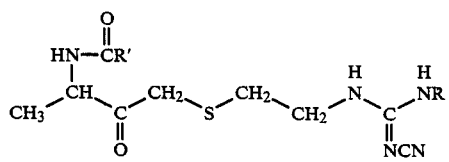

wherein R stands for a lower alkyl group and R' stands for a hydrogen atom or a lower alkyl group.

The cyanoguanidine derivative of the present invention can be prepared by two processes represented by the following reaction formulae.

Process (1)

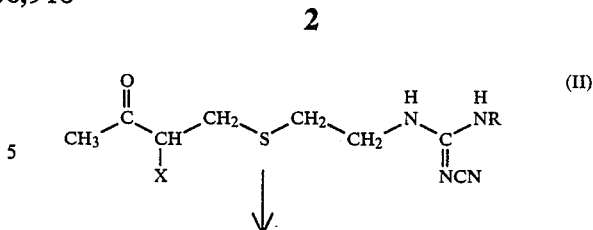

Process (2)

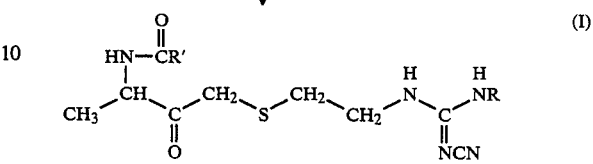

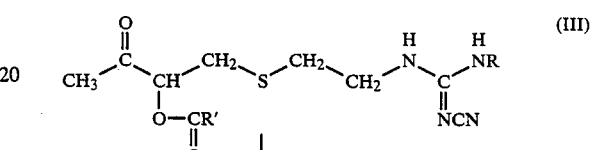

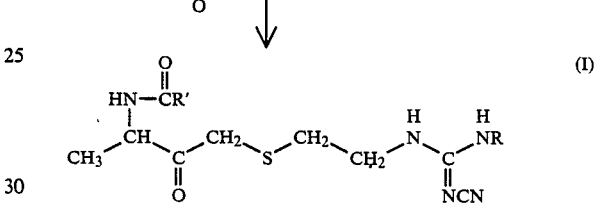

In the above formulae, X stands for a chlorine atom or a bromine atom, and R and R' are as defined above.

The haloketone derivative represented by the formula (II) can be prepared according to the process disclosed in Japanese patent application No. 203640/86, which comprises reacting a methylvinylketone represented by the following formula (IV):

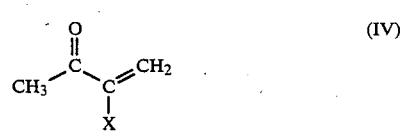

wherein X stands for hydrogen atom, a chlorine atom or a bromine atom, with a mercaptoguanidine derivative represented by the following formula (VI):

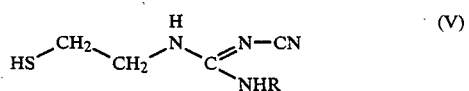

wherein R stands for a lower alkyl group, or reacting an amidinoketone derivative represented by the following formula (VI):

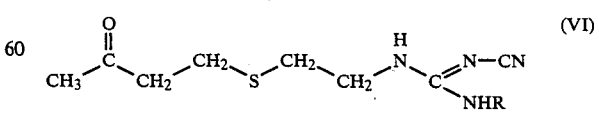

wherein R stands for a lower alkyl group, with a halogenating reagents.

The cyanoguanidine derivative (also called "-acyloxyketone derivative") represented by the formula (III) can be prepared according to the process disclosed in our copending Japanese patent application No. 308538/86, which comprises reacting a haloketone derivative represented by the formula (II) with an anhydrous lower fatty acid salt such as sodium formate, sodium acetate, potassium formate or potassium acetate. This reaction is ordinarily carried out in a solvent, for example, a lower alcohol such as methanol or ethanol, or an amide such as foramide, N,N-dimethylformamide or N-methylformamide, and the anhydrous lower fatty acid salt is added in an amount of 1 to 10 moles per mole of the compound of the formula (II). The reaction is conducted at a temperature of $-20°$ to $150°$ C., preferably $0°$ to $50°$ C., and the reaction is completed within 0.1 to 10 hours.

As the lower alkyl group R in the formulae (II) and (III), there can be mentioned, for example, a methyl group, an ethyl group, an n-propyl group, an isopropyl group, an n-butyl group, a sec-butyl group and an isobutyl group. As the lower alkyl group R', there can be mentioned, for example, a methyl group, an ethyl group, an n-propyl group and an n-butyl group. Compounds in which R is a methyl group and R' is a hydrogen atom and in which R is a methyl group and R' is a methyl group are preferred.

The compound of the formula (II) can be converted to the Cimetidine precursor of the formula (I) by reacting the compound of the formula (II) with an ammonium salt and a lower fatty acid salt.

Furthermore, the compound of the formula (III) can be converted to the Cimetidine precursor of the formula (I) by reacting the compound of the formula (III) with an ammonium salt.

DETAILED DESCRIPTION OF THE PREFERRED EMBODIMENTS

The novel cyanoguanidine derivative represented by the formula (I) can be synthesized from the compound of the formula (II) and the compound of the formula (III) according to the processes represented by the above-mentioned formulae.

The intended compound (I) can be obtained by reacting the compound of the formula (II) with an ammonium salt and a lower fatty acid salt. For this reaction, each of the ammonium salt and lower fatty acid salt is used in an amount of 1 to 10 moles per mole of the compound (II). In the case where the ammonium salt is an ammonium salt of a lower fatty acid (including the case where one salt is used for both the ammonium salt and lower fatty acid salt), it is sufficient if the total amount of both the salts is within the above-mentioned range. As the solvent, there can be singly used alcohols such as methanol, ethanol and isopropanol, lower alkylamides such as N,N-dimethylformamide, N-methylformamide, formamide and acetamide, and ethers such as dioxane. Alternatively, two-layer systems comprising formamide or acetamide and an organic solvent such as chloroform or ethyl acetate can be used as the solvent. Formamide and a two-layer system comprising formamide and chloroform are preferred. The reaction temperature is $0°$ to $100°$ C., preferably $20°$ to $70°$C. The reaction time varies according to the reaction time and is ordinarily in the range of from 10 minutes to 3 days. As the lower fatty acid salt to be used for the reaction, there can be mentioned metal formates such as sodium formate, potassium formate, magnesium formate and calcium formate, alkylammonium formates such as triethylammonium formate and tetrabutylammonium formate, ammonium formate, formamidine formate, metal salts such as sodium acetate, potassium acetate, magnesium acetate, sodium propionate, potassium propionate, sodium butanoate and potassium butanoate, alkylammonium salts such as triethylammonium acetate, triethylammonium propionate and triethylammonium butanoate, and ammonium acetate, ammonium propionate, ammonium butanoate, formamidine acetate and acetamidine acetate. Ammonium salts of weak acids are used as the ammonium salt and as the weak acid, formic acid, acetic acid, carbonic acid and phosphoric acid are mentioned. Ammonium formate is preferably used as the ammonium salt. A dehydrating agent such as methyl orthoformate, ethyl orthoformate or a salt of formamidine may be present in carrying out this reaction.

Furthermore, the intended compound (I) can be obtained by reacting the compound of the formula (III) in the presence of an ammonium salt. In this reaction, the ammonium salt is used in an amount of 1 to 10 moles per mole of the compound (III). As the solvent, there can be singly used alcohols such as methanol, ethanol and isopropanol, lower alkylamides such as N,N-dimethylformamide, N-methylformamide, formamide and acetamide, and ethers such as dioxane. Alternatively, two-layer systems comprising formamide or acetamide and an organic solvent such as chloroform or ethyl acetate can be used. Of these solvents, formamide and a two-layer system comprising formamide and chloroform are preferred. The reaction temperature is $0°$ to $100°$ C., preferably $20°$ to $70°$ C. The reaction time varies according to the reaction temperature and is ordinarily in the range of from 10 minutes to 3 days. An ammonium salt of a weak acid is used as the ammonium salt, and as the weak acid, there can be mentioned formic acid, acetic acid, carbonic acid and formic acid. Ammonium formate, sodium ammonium hydrogenphosphate, triammonium phosphate and diammonium hydrogenphosphate are preferred as the ammonium salt. Furthermore, a dehydrating agent such as methyl orthoformate, ethyl orthoformate or a salt of formamidine may be present in carrying out the reaction.

After the reaction, the intended compound can be isolated by neutralizing the reaction mixture with sodium hydrogencarbonate or the like, removing the solvent under a reduced pressure and refining the residue by customary separating means such as column chromatography.

The cyanoguanidine derivative of the present invention represented by the formula (I) can be easily converted in a high yield to Cimetidine, for example, by reacting the cyanoguanidine derivative in formamide in the presence of ammonium formate, sodium ammonium hydrogenphosphate tetrahydrate and methyl orthoformate at about $100°$ C. according to "PROCESS FOR PREPARATION OF IMIDAZOLE DERIVATIVES" proposed in our copending Japanese patent application No. 32329/87.

The present invention will now be described in detail with reference to the following examples and referential examples.

EXAMPLE 1

Preparation of N-cyano-N'-[2-(3-formamino-2-oxobutylthio)-ethyl]-N''-methylguanidine In 2.5 ml of formamide were dissolved 131 mg of N-[2-(2-chloro-3-oxobutylthio)ethyl]-N'-cyano-N''-methylguanidine and 320 mg of ammonium formate as the ammonium salt and lower fatty acid salt, and the solution was stirred at 50° C. for 1 hour. Then, 420 mg of sodium hydrogencarbonate was added to the solution and formamide was removed under reduced pressure. The obtained residue was refined by silica gel column chromatography (developing solvent: chloroform/ethanol=5/1) to obtain 30 mg of a colorless oily product (the yield was 22%).

$^1$H-NMR Spectrum (CD$_3$OD solvent: ppm):

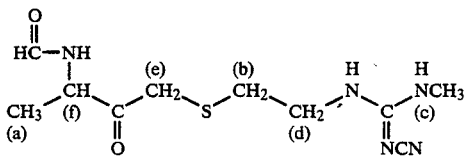

(a) 1.39 (3H, d, J=7), (b) 2.69 (2H, t, J=7), (c) 2.82 (3H, s), (d) 3.40 (2H, t, J=7), (e) 3.59 (2H, s), (f) 4.78 (1H, br.q., J=7), (g) 8.11 (1H, s).

Mass Spectrum: 271 (molecular ion peak).

Thin Layer Chromatography: Rf 0.62 (silica gel TLC Aut. 5715 supplied by Merk, (chloroform/ethanol=4/1).

EXAMPLE 2

Preparation of N-cyano-N'-[2-(3-formylamino-2-oxobutylthio)ethyl]-N''-methylguanidine To 131 mg of N-[2-(2-chloro-3-oxobutylthio)ethyl]-N'-cyano-N''-methylguanidine, 320 mg of ammonium formate, 0.6 ml of methyl orthoformate and 209 mg of sodium ammonium hydrogenphosphate tetrahydrate were added 2.5 ml of formamide and 2.5 ml of chloroform, and the mixture was refluxed for 2 hours. Then, 420 mg of sodium hydrogencarbonate was added to the mixture and the solvent was removed under reduced pressure, and the obtained residue was refined by silica gel column chromatography (developing solvent: ethyl acetate/methanol=10/1) to obtain 28 mg of a colorless oily product (the yield was 21%).

EXAMPLE 3

Preparation of N-cyano-N'-[2-(3-formylamino-2-oxobutylthio)ethyl]-N''-methylguanidine In 2.5 ml of formamide were dissolved 131 mg of N-[2-(2-chloro-3-oxobutylthio)ethyl]-N'-cyano-N''-methylguanidine, 136 mg of sodium formate and 320 mg of ammonium formate, and the solution was stirred at room temperature for 3 days. Then, 420 mg of sodium hydrogencarbonate was added to the solution and formamide was removed under reduced pressure, and the obtained residue was refined by silica gel column chromatography (developing solvent: chloroform/ethanol=5/1) to obtain 28 mg of a colorless oily product (the yield was 19%).

EXAMPLE 4

Preparation of N-cyano-N'-[2-(3-formylamino-2-oxobutylthio)ethyl]-N''-methylguanidine In 1.0 ml of formamide were dissolved 28 mg of N-cyano-N'-[2-(2-formyloxy-3-oxobutylthio)ethyl]-N''-methylguanidine and 25 mg of ammonium formate, and the solution was stirred at 50° C. for 2 hours. Then, 85 mg of sodium hydrogencarbonate was added to the solution and the solvent was removed under reduced pressure, and the obtained residue was refined by silica gel column chromatography (developing solvent: ethyl acetate/methanol=10/1) to obtain 11 mg of a colorless oily product (the yield was 47%).

EXAMPLE 5

Preparation of N-[2-(3-acetamino-2-oxobutylthio)ethyl]-N''-cyano-N''-methylguanidine In 2.5 ml of formamide were dissolved 131 mg of N-[2-(2-chloro-3-oxobutylthio)ethyl]-N'-cyano-N''-methylguanidine and 390 mg of ammonium acetate, and the solution was stirred at 50° C. for 1 hour. Then, 420 mg of sodium hydrogencarbonate was added and the solvent was removed under reduced pressure, and the obtained residue was refined by silica gel column chromatography (developing solvent: chloroform/ethanol=5/1) to obtain 34 mg of a colorless oily product (the yield was 24%).

$^1$H-NMR Spectrum (CD$_3$OD solvent: ppm):

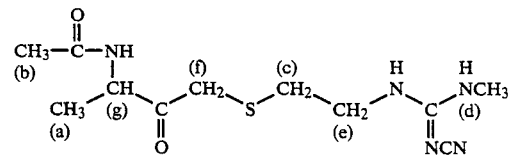

(a) 1.36 (3H, d, J=7), (b) 2.00 (3H, s), (c) 2.70 (2H, t, J=7), (d) 2.83 (3H, s), (e) 3.41 (2H, t, J=7), (f) 3.54 (2H, s), (g) 4.75 (1H, q, J=7).

Mass Spectrum: 285 (molecular ion peak).

Thin Layer Chromatography: Rf 0.69 (silica gel TLC Aut. 5715 supplied by Merk, chloroform/ethanol=4/1).

REFERENTIAL EXAMPLE 1

Preparation of N-cyano-N'-methyl-N''-[2-{(5-methyl-1H-imidazol-4-yl)methylthio}ethyl]guanidine (Cimetidine)

To 136 mg of N-cyano-N'-[2-(3-formylamino-2-oxobutylthio)ethyl]-N''-methylguanidine, 320 mg of amonium formate, 0.6 ml of methyl orthoformate and 209 mg of sodium ammonium hydrogenphosphate tetrahydrate was added 2.5 ml of formamide, and the mixture was stirred at 100° C. for 2 hours. The reaction mixture was cooled and insoluble substances were removed, and the solvent was removed under reduced pressure and the obtained residue was refined by silica gel column chromatography (eluting solvent: chloroform/ethanol=5/1) and recrystallized from isopropanol/ether (60/40) to obtain 100 mg of intended Cimetidine (the yield was 87%).

We claim:

1. A cyanoguanidine derivative represented by the following general formula (I):

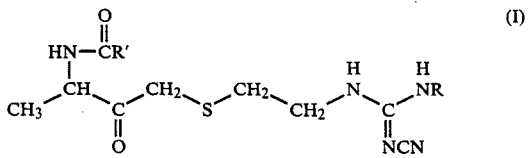

wherein R stands for a lower alkyl group and R' for stands a hydrogen atom or a lower alkyl group.

2. A cyanoguanidine derivative as set forth in claim 1, where R is a methyl group.

3. A cyanoguanidine derivative as set forth in claim 1, wherein R' is a hydrogen atom.

4. A cyanoguanidine derivative as set forth in claim 1, wherein R' is a methyl group.

* * * * *